United States Patent [19]
Messana

[11] Patent Number: 5,277,184
[45] Date of Patent: Jan. 11, 1994

[54] MRI SOUND SYSTEM TRANSDUCER AND HEADSET

[76] Inventor: Russell C. Messana, 237 Redwood Cr., Petaluma, Calif. 94954-3849

[21] Appl. No.: 954,252

[22] Filed: Sep. 30, 1992

[51] Int. Cl.⁵ ............................................. A61B 5/055
[52] U.S. Cl. ........................... 128/653.5; 324/318; 381/88; 381/188; 381/205; 381/109
[58] Field of Search .......................... 128/653.2, 653.5; 324/300, 309, 318; 381/87, 88, 90, 109 187-190, 205, 59

[56] References Cited

U.S. PATENT DOCUMENTS

| | | | |
|---|---|---|---|
| Re. 34,219 | 4/1993 | Lederer | 381/90 |
| 4,347,911 | 9/1982 | Bertagna et al. | 181/130 |
| 4,654,871 | 3/1987 | Chaplin et al. | 381/72 |
| 4,701,952 | 10/1987 | Taylor | 381/67 |
| 4,807,294 | 2/1989 | Iwata et al. | 381/190 |
| 5,076,275 | 12/1991 | Bechor et al. | 128/653.2 |
| 5,133,017 | 7/1992 | Cain et al. | 381/71 |

Primary Examiner—Lee S. Cohen
Assistant Examiner—Krista M. Pfaffle
Attorney, Agent, or Firm—Larry D. Johnson

[57] ABSTRACT

A MRI sound system transducer and headset provides music and operator communication for the Magnetic Resonance Imaging (MRI) patient. The inventive system includes a pneumatic, non-magnetic transducer which converts electrical output from a music source or operator microphone to moving air, and delivers this pneumatic audio signal through plastic tubes inside the high magnetic field area to a headset which attenuates the ambient noise in the area.

7 Claims, 2 Drawing Sheets

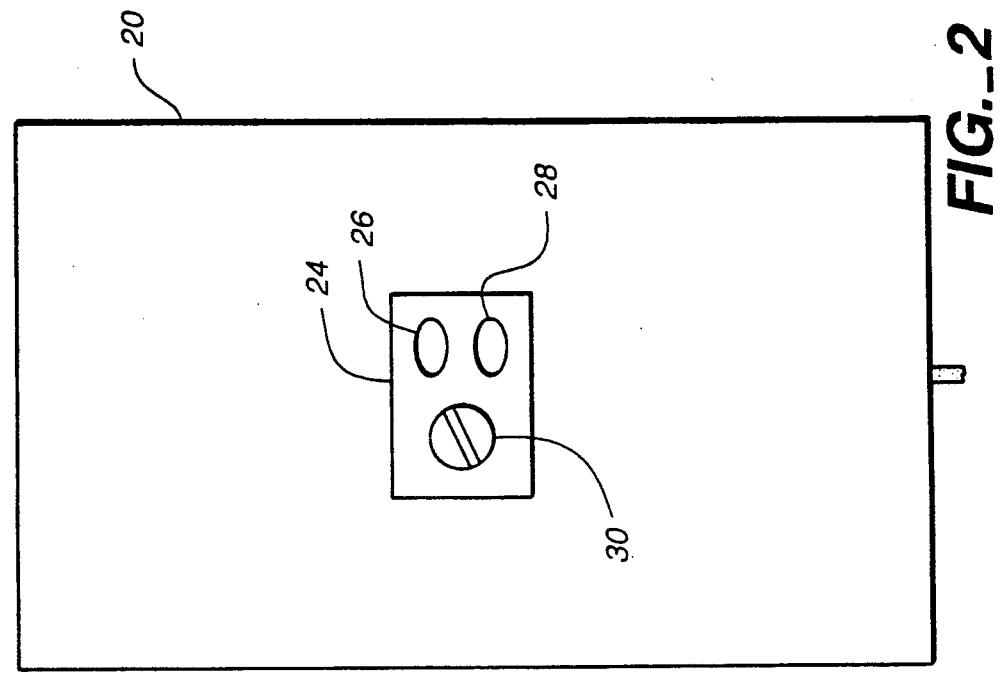
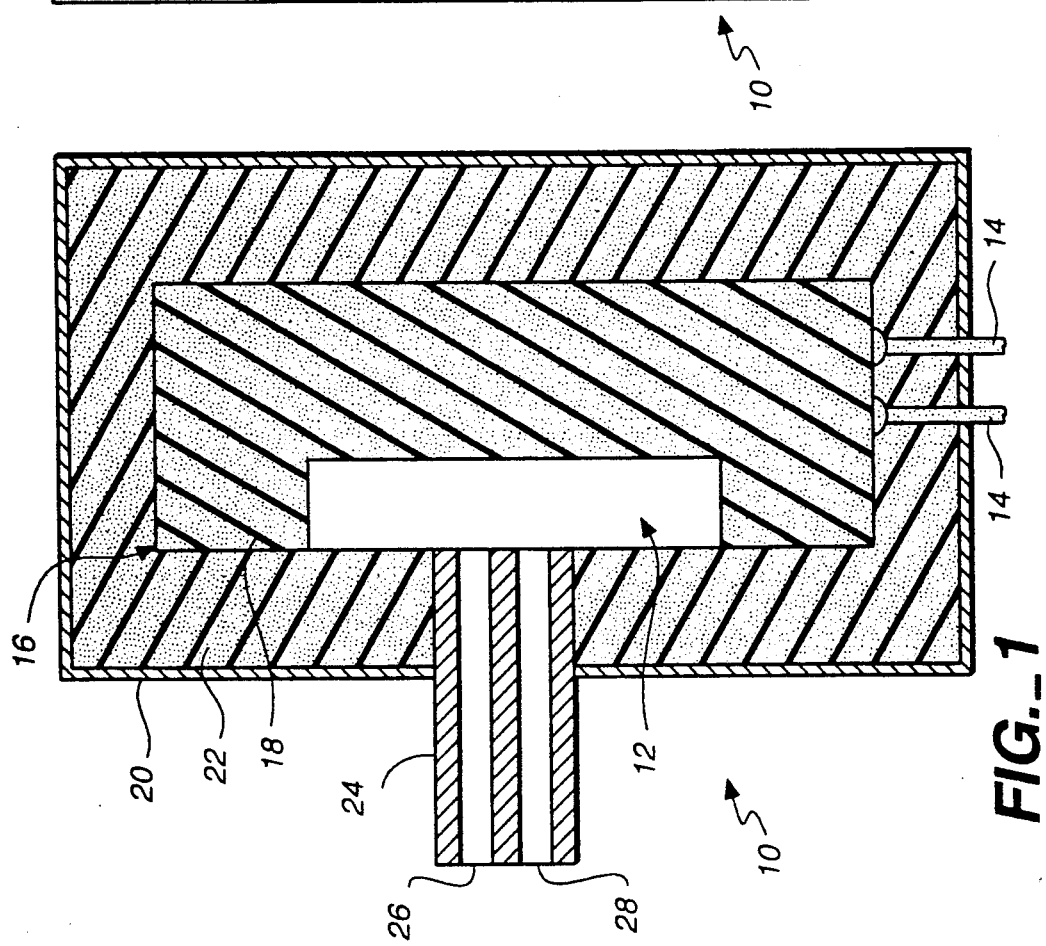

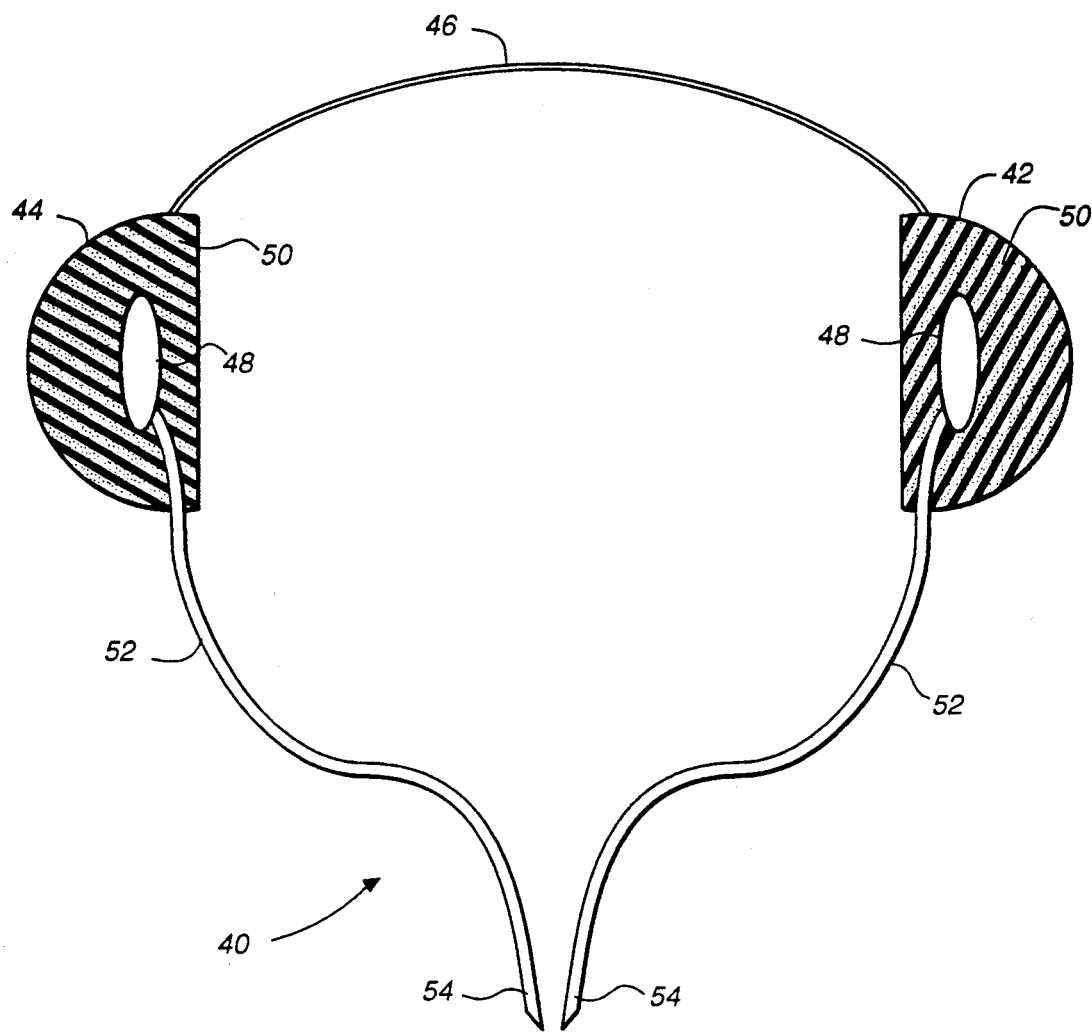
FIG._3

MRI SOUND SYSTEM TRANSDUCER AND HEADSET

BACKGROUND OF THE INVENTION

1. Field of the Invention

This invention relates generally to audio sound systems and headsets, and more specifically to an improved non-magnetic audio sound system and headset apparatus for use in high magnetic field environments such as those created in a magnetic resonance imaging apparatus.

2. Description of the Prior Art

Magnetic Resonance Imaging (MRI) scans are a valuable medical diagnostic tool, and are now in widespread use. However, due to the noise and lack of any visual stimulation (the patient is lying in a narrow tube), many patients don't enjoy the experience of an MRI scan. Thus, it is desirable to provide music or other audio stimulation to the patient during their scan. Unfortunately, MRI magnets create a high magnetic field in the ambient area, which is problematic for standard audio systems. In addition, the noise gradients generated during an MRI scan are very loud, necessitating some form of attenuation of the noise level down to a comfortable level.

SUMMARY OF THE INVENTION

The MRI sound system transducer and headset of this invention is a system to provide music and operator communication for the Magnetic Resonance Imaging (MRI) patient. The inventive system includes a pneumatic, non-magnetic transducer which converts the electrical output from a music source or operator microphone to moving air, and delivers this pneumatic audio signal through plastic tubes to a headset inside the high magnetic field area. The custom headset attenuates the noise in the area by up to 25 db while enabling the music and/or communications from the MRI operator at all times.

The inventive transducer incorporates a piezoelectric speaker enclosed in an aluminum or other non-ferrous box enclosure, with that assembly being enclosed in a second non-ferrous box for further soundproofing. All parts are non-magnetic. BNC type connectors are used to connect the audio source (tape player, CD player, microphone, etc.) to the speaker within the boxes using RG-222 or RG-59 shielded cable. A block of aluminum or other non-ferrous material is used to provide a wave guide from the piezoelectric speaker in the boxes to the plastic tubing for the headset.

The purpose of the transducer is to provide a music source within the room, near the MRI magnet and the patient, thereby requiring only a short run of plastic tubing out to the headset. This shorter run is capable of giving better sound quality. Sometimes the sound through a plastic tubing gives too much bass sound. To insure sound quality, the piezoelectric speaker can be dampened by adjusting a tone control screw. This screw produces pressure on the speaker diaphragm which reduces the bass sound from the transducer.

The inventive headset attenuates gradient sound from the MRI magnet while allowing music/voice sounds inside the headset via the plastic tubing from the transducer. A construction-type headset (filled with sound-deadening material) is modified such that the normal ear pieces of an airline-type headset (utilizing standard pneumatic sound chambers) are installed inside the construction headset. A hole is drilled in the bottom of each sound-attenuating cover of the construction headset. A rubber fitting is installed to secure the plastic tubing to be installed and protect it from vibrations of the headset outer case. The end connector of the plastic tubing is either male or female depending on the output holes from the transducer in the room. All construction is of nonmetal type material. Sanitation covers for each ear piece may be provided.

BRIEF DESCRIPTION OF THE DRAWINGS

FIG. 1 is a side elevation cross-sectional view of the MRI sound system transducer of this invention, illustrating a piezoelectric speaker including its electrical connections, an inner non-magnetic box enclosure filled with sound deadening material, an outer non-magnetic box enclosure similarly filled with sound deadening material, and a transducer waveguide including a pair of pneumatic audio ports;

FIG. 2 is a front elevation view of the MRI sound system transducer of this invention illustrating the outer non-magnetic box enclosure, the transducer waveguide, the pair of pneumatic audio ports, and a speaker tone control screw; and FIG. 3 is a front elevation view in partial cross-section of the modified headset of the MRI sound system of this invention, illustrating right and left ear covers joined by a headset strap, each cover including a sound chamber surrounded by sound deadening material, a length of pneumatic audio tubing, and a pneumatic audio connector for attachment to the pneumatic audio port of the transducer waveguide.

DETAILED DESCRIPTION OF A PREFERRED EMBODIMENT

FIG. 1 is a side elevation cross-sectional view of the MRI sound system transducer 10 of this invention, illustrating a piezoelectric speaker 12 including its electrical connections 14, an inner non-magnetic box enclosure 16 filled with sound deadening material 18, an outer non-magnetic box enclosure 20 similarly filled with sound deadening material 22, and a transducer waveguide 24 including a pair of pneumatic audio ports 26, 28. Waveguide 24 and audio ports 26, 28 are preferably made in dimensions to provide a six to one length to port diameter ratio, e.g., approximately one-and-a-half inches long with ports approximately one-quarter inch in diameter. Waveguide 24 is preferably made of aluminum, brass or other non-ferrous material.

FIG. 2 is a front elevation view of the MRI sound system transducer 10 of FIG. 1, illustrating the outer non-magnetic box enclosure 20, the transducer waveguide 24, a pair of pneumatic audio ports 26, 28, and a speaker tone control screw 30. This tone control screw may comprise a one-quarter/twenty non-ferrous screw that can be turned to contact and dampen the piezoelectric speaker diaphragm within.

FIG. 3 is a front elevation view in partial cross-section of the modified headset 40 of the MRI sound system of this invention, illustrating right and left ear covers 42, 44 joined by a headset strap 46, each cover including a sound chamber 48 surrounded by sound deadening material 50, a length of pneumatic audio tubing 52, and a pneumatic audio connector 54 (male or female, as needed) for attachment to the pneumatic audio ports 26, 28 of the transducer waveguide (FIGS. 1 and 2).

The sound chambers 48 provide normal sound to the patient's ears, while the sound deadening material reduces the ambient noise gradient of the MRI equipment. By placing the (non-magnetic) transducer in the immediate area of the patient and the MRI equipment, the length of tubing 52 can be kept to a minimum (e.g., ten to thirty-six inches long).

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A sound system for a patient in a MRI apparatus, said sound system comprising:
   a piezoelectric speaker;
   a first enclosure member housing said piezoelectric speaker;
   a second enclosure member housing said piezoelectric speaker and said first enclosure member;
   a transducer waveguide portion adjacent said piezoelectric speaker and extending through said first enclosure member and said second enclosure member, said tranducer waveguide portion including a tone control screw to selectively dampen said piezoelectric speaker;
   a pair of pneumatic audio ports in said transducer waveguide portion;
   a headset portion including a pair of ear covers, each ear cover including a sound chamber surrounded by sound deadening material; and
   a length of pneumatic audio tubing connecting said headset sound chambers to said pneumatic audio ports.

2. The sound system of claim 1 wherein said first enclosure member housing said piezoelectric speaker includes a sound deadening material.

3. The sound system of claim 1 wherein said second enclosure member housing said piezoelectric speaker includes a sound deadening material.

4. The sound system of claim 1 wherein said transducer waveguide portion is constructed in a length to audio port diameter ratio of approximately six to one.

5. The sound system of claim 1 wherein said first and second enclosure members are constructed of a non-ferrous material.

6. The sound system of claim 1 wherein said transducer waveguide portion is constructed of a non-ferrous material.

7. The sound system of claim 1 wherein said headset portion is constructed of a non-ferrous material.

* * * * *